United States Patent
Chapa et al.

(10) Patent No.: US 8,918,182 B2
(45) Date of Patent: Dec. 23, 2014

(54) METHODS AND SYSTEMS FOR AUTOMATICALLY DETERMINING AN IMPLANT SIDE ASSOCIATED WITH A COCHLEAR IMPLANT

(75) Inventors: Fernando Chapa, Harold, CA (US); Guillermo A. Calle, Moorpark, CA (US); Tracey L. Kruger, Valencia, CA (US); Jacob Johnston, Winnetka, CA (US)

(73) Assignee: Advanced Bionics AG, Staefa (CH)

( * ) Notice: Subject to any disclaimer, the term of this patent is extended or adjusted under 35 U.S.C. 154(b) by 581 days.

(21) Appl. No.: 12/871,867

(22) Filed: Aug. 30, 2010

(65) Prior Publication Data

US 2012/0053656 A1 Mar. 1, 2012

(51) Int. Cl.
*A61N 1/00* (2006.01)
*H04R 25/00* (2006.01)
*A61N 1/36* (2006.01)

(52) U.S. Cl.
CPC ............ *H04R 25/70* (2013.01); *A61N 1/36032* (2013.01); *H04R 25/552* (2013.01)
USPC .......................................................... 607/57

(58) Field of Classification Search
USPC .................................................... 607/55–57
See application file for complete search history.

(56) References Cited

U.S. PATENT DOCUMENTS

| | | | |
|---|---|---|---|
| 6,895,280 B2 * | 5/2005 | Meadows et al. ............... | 607/46 |
| 2006/0098831 A1 | 5/2006 | Kaiser et al. | |
| 2007/0106345 A1 | 5/2007 | Seligman | |
| 2007/0135862 A1 * | 6/2007 | Nicolai et al. .................. | 607/56 |
| 2007/0230711 A1 * | 10/2007 | Hasler et al. .................... | 381/58 |
| 2009/0306742 A1 * | 12/2009 | Van Dijk et al. ................ | 607/57 |
| 2010/0067707 A1 | 3/2010 | Schwerdtner | |

OTHER PUBLICATIONS

International Search Report and Written Opinion received in International Application No. PCT/US2011/045678, dated Oct. 21, 2011.

* cited by examiner

*Primary Examiner* — Scott Getzow
(74) *Attorney, Agent, or Firm* — ALG Intellectual Property, LLC

(57) ABSTRACT

An exemplary method includes a fitting subsystem detecting a communicative coupling of a cochlear implant associated with a patient to a sound processor connected to the fitting subsystem and automatically determining, in response to the communicative coupling, an implant side associated with the cochlear implant in accordance with one or more implant side selection factors. Corresponding methods and systems are also described.

24 Claims, 15 Drawing Sheets

Fig. 9

METHODS AND SYSTEMS FOR AUTOMATICALLY DETERMINING AN IMPLANT SIDE ASSOCIATED WITH A COCHLEAR IMPLANT

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea, which are needed to transduce acoustic signals into auditory nerve impulses. People who suffer from sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers by way of one or more channels formed by an array of electrodes implanted in the cochlea. Direct stimulation of the auditory nerve fibers leads to the perception of sound in the brain and at least partial restoration of hearing function.

When a cochlear implant is initially implanted in a patient, and during follow-up tests and checkups thereafter, it is usually necessary to "fit" the cochlear implant to the patient. To this end, an implant record associated with the cochlear implant may be created and stored by a fitting system. The implant record may specify an implant side associated with the cochlear implant. In other words, the implant record may specify the ear (i.e., the right ear or the left ear) with which the cochlear implant is associated. It is important for the implant side information maintained by the implant record to be accurate—especially in the case of a bilateral cochlear implant patient (i.e., a patient who has a separate cochlear implant for each ear). However, because the implant side information has heretofore been input manually, human error may occasionally result in implant records having erroneous implant side information.

SUMMARY

An exemplary method includes a fitting subsystem detecting a communicative coupling of a cochlear implant associated with a patient to a sound processor connected to the fitting subsystem and automatically determining, in response to the communicative coupling, an implant side associated with the cochlear implant in accordance with one or more implant side selection factors.

Another exemplary method includes a fitting subsystem detecting a communicative coupling of a cochlear implant associated with a patient to a sound processor connected to the fitting subsystem, automatically selecting an implant side of the cochlear implant in accordance with one or more implant side selection factors, automatically populating an implant record associated with the cochlear implant with data representative of the selected implant side, and presenting information indicative of the selected implant side within a graphical user interface.

An exemplary system includes a detection facility configured to detect a communicative coupling of a cochlear implant associated with a patient to a sound processor connected to a fitting station and an implant side management facility communicatively coupled to the detection facility and configured to automatically determine, in response to the communicative coupling, an implant side associated with the cochlear implant in accordance with one or more implant side selection factors.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 9 illustrates an exemplary graphical user interface ("GUI") that may be configured to facilitate manual creation of an implant record according to principles described herein.

DETAILED DESCRIPTION

Methods and systems for automatically determining an implant side associated with a cochlear implant are described herein. As described in more detail below, a fitting subsystem may be configured to detect a communicative coupling of a cochlear implant associated with a patient to a sound processor connected to the fitting subsystem and automatically determine, in response to the communicative coupling, an implant side associated with the cochlear implant in accordance with one or more implant side selection factors.

As used herein, an "implant side" associated with a cochlear implant refers to a particular ear (i.e., the right ear or the left ear) associated with the cochlear implant. Hence, a cochlear implant used to provide a sensation of sound to the right ear has an associated "right implant side." Likewise, a cochlear implant used to provide a sensation of sound to the left ear has an associated "left implant side."

As used herein, "side implant side selection factors" may include any factor associated with one or more cochlear implants associated with a patient, one or more implant records associated with a patient, one or more default parameters, one or more actions performed by a user of the fitting subsystem, and/or any other factor as may serve a particular implementation.

In some examples, the fitting subsystem may be further configured to automatically populate an implant record associated with the cochlear implant with data representative of the determined implant side. As used herein, an "implant record" refers to a data record or the like that is descriptive of a particular cochlear implant. For example, an implant record may include information descriptive of an implant side, a type, a unique identifier (e.g., an electronic serial number), and/or any other information associated with a particular cochlear implant as may serve a particular implementation. An implant record may be "unassociated" or "associated." An unassociated implant record has not yet been populated with a unique identifier associated with a cochlear implant (which populating typically occurs the first time that the cochlear implant communicatively couples to a sound processor connected to the fitting subsystem). Conversely, an "associated" implant record has been populated with the unique identifier. An implant record may additionally be "inactive" or "active." An "inactive" implant record has been marked as corresponding to an explanted cochlear implant. Conversely, an "active" implant record has been marked as corresponding to an explanted cochlear implant.

Figure 1:
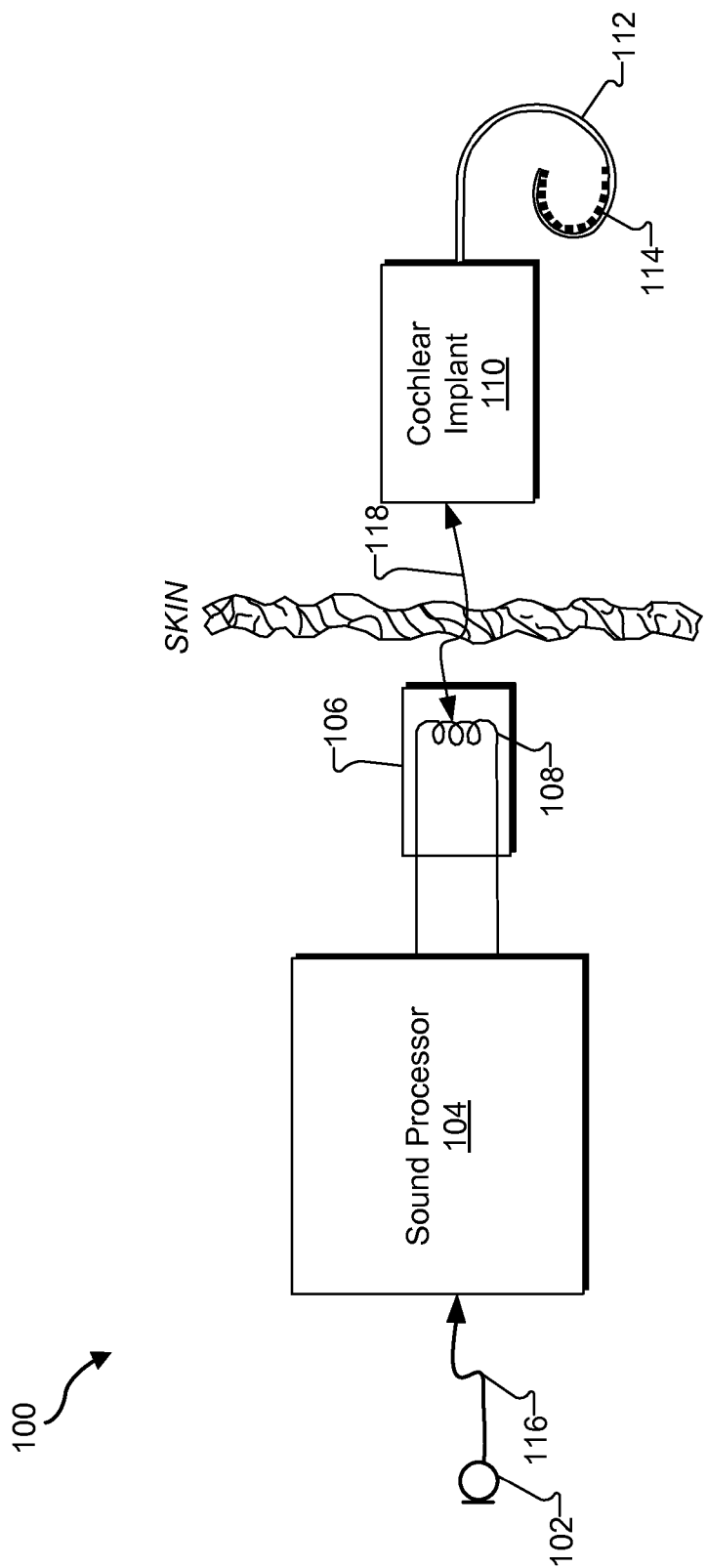
FIG. 1 illustrates an exemplary cochlear implant system according to principles described herein.

To facilitate an understanding of the methods and systems described herein, an exemplary cochlear implant system 100 will be described in connection with FIG. 1. As shown in FIG. 1, cochlear implant system 100 may include a microphone 102, a sound processor 104, a headpiece 106 having a coil 108 disposed therein, a cochlear implant 110 (also referred to as an "implantable cochlear stimulator"), and a lead 112 with a plurality of electrodes 114 disposed thereon. Additional or alternative components may be included within cochlear implant system 100 as may serve a particular implementation.

As shown in FIG. 1, microphone 102, sound processor 104, and headpiece 106 may be located external to a cochlear implant patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct cochlear implant 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing strategy to generate appropriate stimulation parameters for controlling cochlear implant 110. Sound processor 104 may include or be implemented by a behind-the-ear ("BTE") unit, a portable speech processor ("PSP"), and/or any other sound-processing unit as may serve a particular implementation. Exemplary components of sound processor 104 will be described in more detail below.

Sound processor 104 may be configured to transcutaneously transmit, in accordance with a sound processing program associated with cochlear implant 110, one or more control parameters and/or one or more power signals to cochlear implant 110 with coil 108 by way of a communication link 118. These control parameters may be configured to specify one or more stimulation parameters, operating parameters, and/or any other parameter by which cochlear implant 110 is to operate as may serve a particular implementation. Exemplary control parameters include, but are not limited to, stimulation current levels, volume control parameters, program selection parameters, operational state parameters (e.g., parameters that turn a sound processor and/or a cochlear implant on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels ("T levels"), channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within cochlear implant 110. In this manner, control parameters and power signals may be wirelessly transmitted between sound processor 104 and cochlear implant 110 via communication link 118. It will be understood that data communication link 118 may include a bi-directional communication link and/or one or more dedicated uni-directional communication links. In some alternative embodiments, sound processor 104 and cochlear implant 110 may be directly connected with one or more wires or the like.

Cochlear implant 110 may be configured to generate electrical stimulation representative of an audio signal detected by microphone 102 in accordance with one or more stimulation parameters transmitted thereto by sound processor 104. Cochlear implant 110 may be further configured to apply the electrical stimulation to one or more stimulation sites within the cochlea via one or more electrodes 114 disposed along lead 112. In some examples, cochlear implant 110 may include a plurality of independent current sources each associated with a channel defined by one or more of electrodes 114. In this manner, different stimulation current levels may be applied to multiple stimulation sites simultaneously by way of multiple electrodes 114. In such examples, cochlear implant system 100 may be referred to as a "multi-channel cochlear implant system."

To facilitate application of the electrical stimulation generated by cochlear implant 110, lead 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the stimulation site. Any number of electrodes 114 (e.g., sixteen) may be disposed on lead 112 as may serve a particular implementation.

Figure 2:
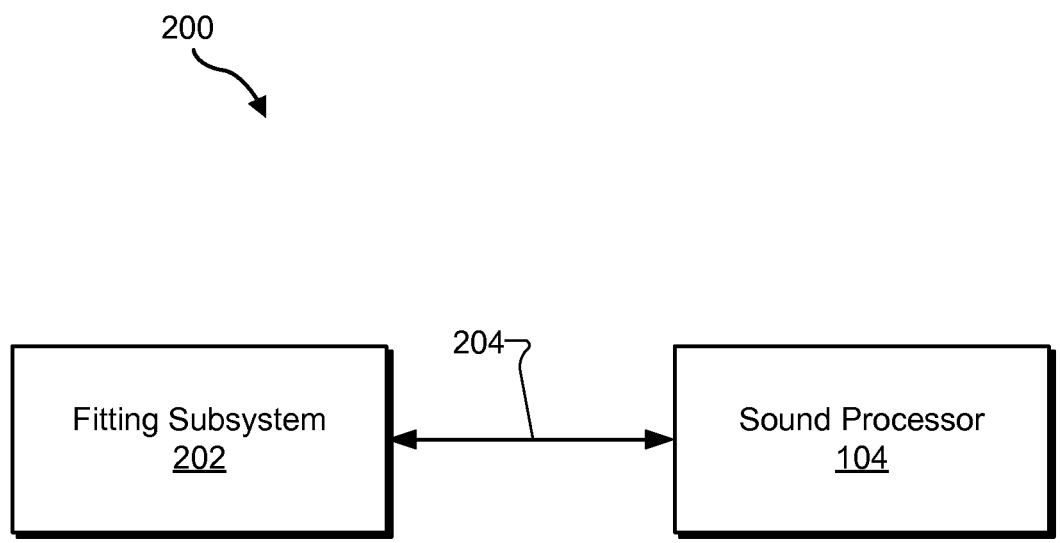
FIG. 2 illustrates an exemplary cochlear implant fitting system according to principles described herein.

FIG. 2 illustrates an exemplary cochlear implant fitting system 200 (or simply "fitting system 200") that may be used to fit a cochlear implant patient. As used herein, the terms "fitting a cochlear implant patient" and "fitting a cochlear implant to a patient" will be used interchangeably to refer to performing one or more fitting operations associated with sound processor 104, cochlear implant 110, and/or any other component of cochlear implant system 100 in order to optimize performance of cochlear implant system 100 for the patient. Such fitting operations may include, but are not limited to, adjusting one or more control parameters by which sound processor 104 and/or cochlear implant 110 operate, measuring one or more electrode impedances, performing one or more neural response detection operations, and/or performing one or more diagnostics procedures associated with the cochlear implant system.

As shown in FIG. 2, fitting system 200 may include a fitting subsystem 202 configured to be selectively and communicatively coupled to sound processor 104 of cochlear implant system 100 by way of a communication link 204. Fitting subsystem 202 and sound processor 104 may communicate using any suitable communication technologies, devices, networks, media, and protocols supportive of data communications.

Fitting subsystem 202 may be configured to perform one or more of the fitting operations described herein. To this end, fitting subsystem 202 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation. An exemplary implementation of fitting subsystem 202 will be described in more detail below.

Figure 3:
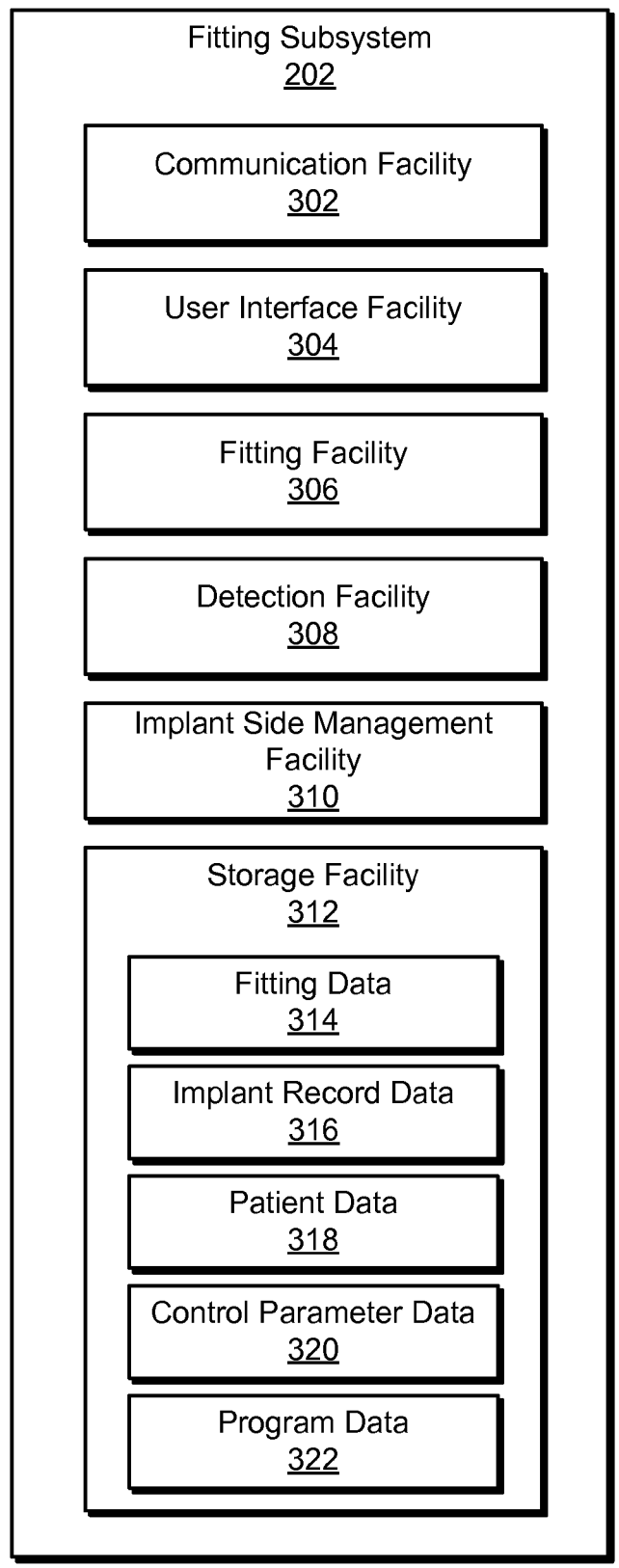
FIG. 3 illustrates exemplary components of an exemplary fitting subsystem according to principles described herein.

FIG. 3 illustrates exemplary components of fitting subsystem 202. As shown in FIG. 3, fitting subsystem 202 may include a communication facility 302, a user interface facility 304, a fitting facility 306, a detection facility 308, an implant side management facility 310, and a storage facility 312, which may be communicatively coupled to one another using any suitable communication technologies. Each of these facilities will now be described in more detail.

Communication facility 302 may be configured to facilitate communication between fitting subsystem 202 and cochlear implant system 100 (e.g., sound processor 104 and/or cochlear implant 110). For example, communication facility 302 may be implemented by a CPI device, which may include any suitable combination of components configured to allow fitting subsystem 202 to interface and communicate with sound processor 104. Communication facility 302 may additionally or alternatively include one or more transceiver components configured to wirelessly transmit data (e.g., program data and/or control parameter data) to sound processor 104 and/or wirelessly receive data (e.g., feedback data, impedance measurement data, neural response data, etc.) from sound processor 104.

In some examples (e.g., during a fitting of a bilateral cochlear implant patient), communication facility 302 may facilitate selective and/or concurrent communication between multiple sound processors (e.g., right and left sound processors). In this manner, communication facility 302 may be configured to communicate with a first cochlear implant associated with a first ear (e.g., the right ear) of the patient by way of a first sound processor and a second cochlear implant associated with a second ear (e.g., the left ear) of the patient by way of a second sound processor.

Communication facility 302 may additionally or alternatively be configured to facilitate communication between fitting subsystem 202 and one or more other devices. For example, communication facility 302 may be configured to facilitate communication between fitting subsystem 202 and one or more computing devices (e.g., by way of the Internet and/or one or more other types of networks), reference implants, and/or any other computing device as may serve a particular implementation.

User interface facility 304 may be configured to provide one or more user interfaces configured to facilitate user interaction with fitting subsystem 202. For example, user interface facility 304 may provide a graphical user interface ("GUI") through which one or more functions, options, features, and/or tools associated with one or more fitting operations described herein may be provided to a user and through which user input may be received. In certain embodiments, user interface facility 304 may be configured to provide the GUI to a display device (e.g., a computer monitor) for display. In some examples, as will be described in more detail below, user interface facility 304 may be configured to provide one or more GUIs that are configured to facilitate creation and/or management of one or more implant records and/or present information indicative of an automatically determined implant side associated with a cochlear implant.

Fitting facility 306 may be configured to perform one or more fitting operations. For example, fitting facility 306 may be configured to adjust one or more control parameters by which sound processor 104 and/or cochlear implant 110 operate, direct sound processor 104 to measure one or more electrode impedances, perform one or more neural response detection operations, and/or perform one or more diagnostics procedures associated with cochlear implant system 100.

Detection facility 308 may be configured to detect a communicative coupling of a cochlear implant (e.g., cochlear implant 110) to a sound processor (e.g., sound processor 104) connected to fitting subsystem 202. The detection may be made in any suitable way. For example, detection facility 308 may be configured to detect a signal transmitted thereto by the cochlear implant when the cochlear implant "locks" to the sound processor.

Implant side management facility 310 may be configured to automatically determine, in response to a communicative coupling of a cochlear implant to a sound processor connected to fitting subsystem 202, an implant side associated with the cochlear implant in accordance with one or more implant side selection factors. Such implant side selection factors may include any factor associated with one or more other cochlear implants associated with the patient, one or more implant records associated with the patient, one or more default parameters, one or more actions performed by a user of fitting subsystem 202, and/or any other factor as may serve a particular implementation. Various ways in which implant side management facility 310 may use the implant side factors to automatically determine an implant side associated with a cochlear implant will be described in more detail below.

In some examples, after automatically determining an implant side associated with a cochlear implant, implant side management facility 310 may be further configured to automatically populate an implant record associated with the cochlear implant with data representative of the determined implant side. As will be described in more detail below, information representative of the determined implant side may be presented to a user of fitting subsystem 202, who may override the determined implant side by selecting a different implant side to be associated with the cochlear implant.

Storage facility 312 may be configured to maintain fitting data 314 associated with one or more fitting operations, implant record data 316 representative of one or more implant records associated with one or more cochlear implants, patient data 318 representative of data descriptive of or otherwise associated with one or more cochlear implant patients, control parameter data 320 representative of one or more control parameters, and program data 322 representative of one or more sound processing programs, any or all of which may be maintained within one or more data sets. Storage facility 312 may be configured to maintain additional or alternative data as may serve a particular implementation.

Figure 4:
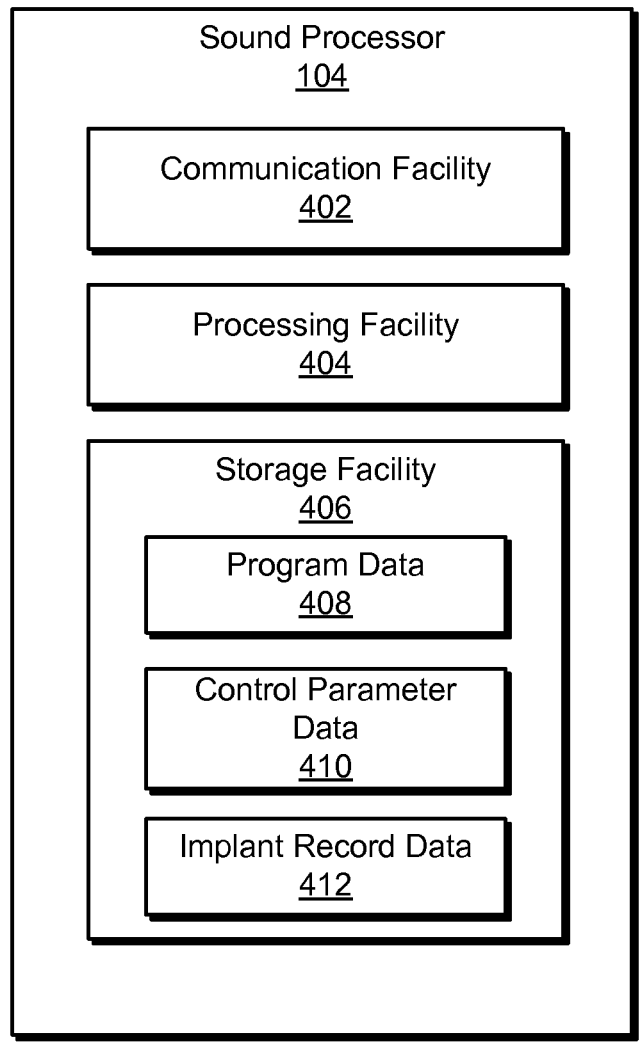
FIG. 4 illustrates exemplary components of a sound processor according to principles described herein.

FIG. 4 illustrates exemplary components of sound processor 104. As shown in FIG. 4, sound processor 104 may include a communication facility 402, a processing facility 404, and a storage facility 406, any or all of which may be in communication with one another using any suitable communication technologies. Each of these facilities will now be described in more detail.

Communication facility 402 may be configured to facilitate communication between sound processor 104 and fitting subsystem 202. For example, communication facility 402 may be configured to facilitate electrical coupling of sound processor 104 to a CPI device in order to communicate with fitting subsystem 202. Communication facility 402 may be further configured to facilitate communication between sound processor 104 and cochlear implant 110. For example, communication facility 402 may include transceiver components configured to wirelessly transmit data (e.g., control parameters and/or power signals) to cochlear implant 110 and/or wirelessly receive data from cochlear implant 110.

Processing facility 404 may be configured to perform one or more signal processing heuristics on an audio signal presented to the patient. For example, processing facility 404 may perform one or more pre-processing operations, spectral analysis operations, noise reduction operations, mapping operations, and/or any other types of signal processing operations on a detected audio signal as may serve a particular implementation. In some examples, processing facility 404 may generate and/or adjust one or more control parameters governing an operation of cochlear implant 110 (e.g., one or more stimulation parameters defining the stimulation pulses to be generated and applied by cochlear implant 110). In some examples, processing facility 404 may be configured to operate in accordance with one or more sound processing programs provided by fitting subsystem 202 and/or otherwise stored within storage facility 406.

Storage facility 406 may be configured to maintain program data 408 representative of one or more sound processing programs, control parameter data 410 representative of one or more control parameters, and implant record data 412 representative of an implant record associated with one or more cochlear implants associated with sound processor 104. Storage facility 406 may be configured to maintain additional or alternative data as may serve a particular implementation.

Figure 5:
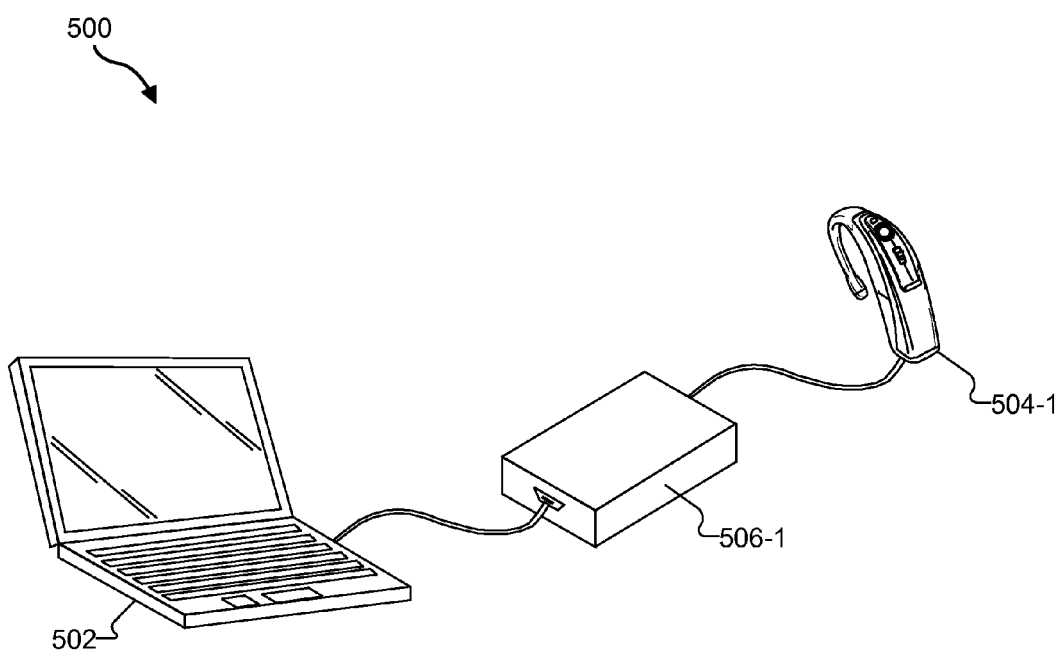
FIG. 5 illustrates an exemplary implementation of the cochlear implant fitting system of FIG. 2 according to principles described herein.

FIG. 5 illustrates an exemplary implementation 500 of fitting system 200. In implementation 500, a fitting station 502 may be selectively and communicatively coupled to a sound processor 504-1 by way of a CPI device 506-1. Sound processor 504-1 is depicted in the form of a BTE unit for illustrative purposes only. Fitting station 502 may be selectively and communicatively coupled to any other type of sound processor as may serve a particular implementation.

Fitting station 502 may include any suitable computing device and/or combination of computing devices and be configured to at least partially implement fitting subsystem 202 by performing one or more of the fitting operations described herein. For example, fitting station 502 may display one or more GUIs configured to facilitate selection of one or more measurements to perform using sound processor 504-1, selection of one or more sound processing programs by which sound processor 504-1 operates, adjustment of one or more control parameters by which sound processor 504-1 operates, management of one or more implant records associated with a cochlear implant that is associated with sound processor 504-1, and/or any other fitting operation as may serve a particular implementation. Fitting station 502 may be utilized by an audiologist, a clinician, and/or any other user to fit one or more cochlear implants to a patient using sound processor 504-1.

Sound processor 504-1 may be configured to selectively and communicatively couple to one or more cochlear implants. In this manner, sound processor 504-1 may be configured to facilitate the fitting of the one or more cochlear implants by fitting station 502.

CPI device 506-1 may be configured to facilitate communication between fitting station 502 and sound processor 504-1. In some examples, CPI device 506-1 may be selectively and communicatively coupled to fitting station 502 and/or sound processor 504-1 by way of one or more ports included within fitting station 502 and sound processor 504-1.

In some examples, implementation 500 may be used to fit right and left cochlear implants to a bilateral cochlear implant patient. For example, each cochlear implant may be alternatingly coupled to sound processor 504-1 so that fitting station 502 may perform one or more fitting operations on the left and right cochlear implants.

Figure 6:
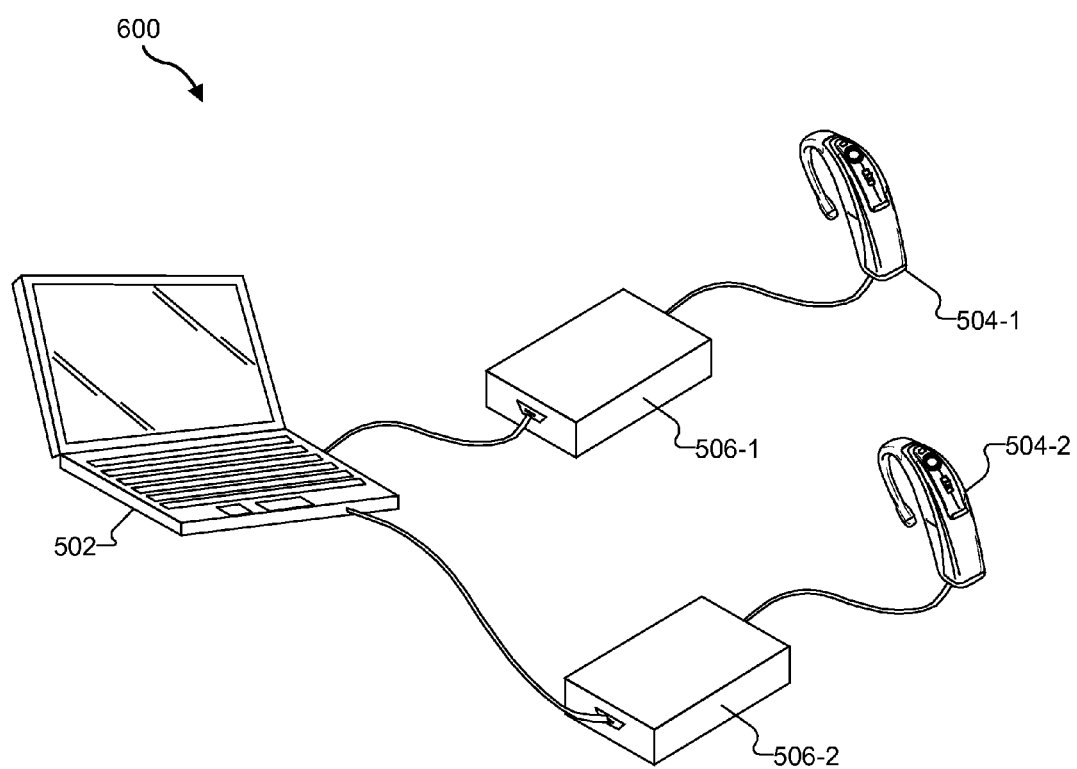
FIG. 6 illustrates another exemplary implementation of the cochlear implant fitting system of FIG. 2 according to principles described herein.

FIG. 6 illustrates an exemplary alternative implementation 600 of fitting system 200 that may be used to fit a bilateral cochlear implant patient. In implementation 600, a fitting station 502 may be selectively and communicatively coupled to first and second sound processors 504-1 and 504-2 (collectively referred to herein as "sound processors 504") by way of corresponding CPI devices 506-1 and 506-2 (collectively referred to herein as "CPI devices 506"). Sound processor 504-1 may be associated with a first cochlear implant (e.g., a cochlear implant associated with a right ear of a patient) and sound processor 504-2 may be associated with a second cochlear implant (e.g., a cochlear implant associated with a left ear of the patient).

Figure 7:
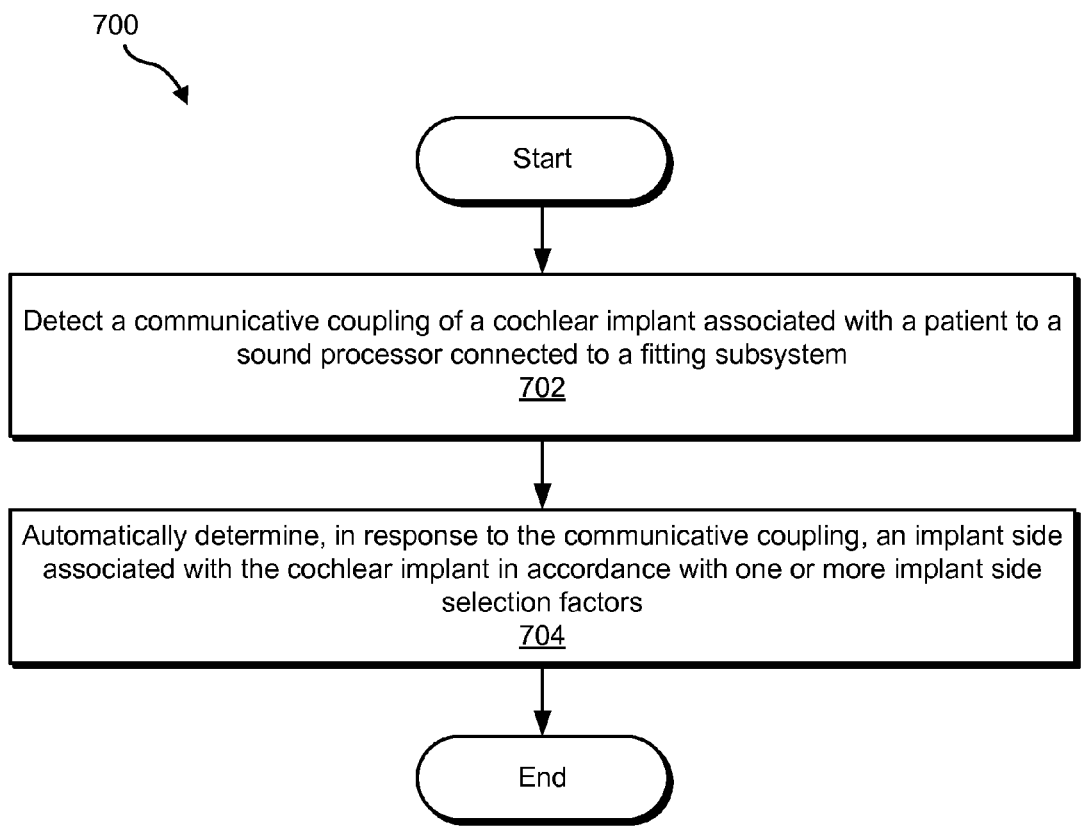
FIG. 7 illustrates an exemplary method of automatically determining an implant side associated with a cochlear implant according to principles described herein.

FIG. 7 illustrates an exemplary method 700 of automatically determining an implant side associated with a cochlear implant. While FIG. 7 illustrates exemplary steps according to one embodiment, other embodiments may omit, add to, reorder, and/or modify any of the steps shown in FIG. 7. One or more of the steps shown in FIG. 7 may be performed by any component or combination of components of fitting subsystem 202 and/or fitting station 502.

In step 702, a fitting subsystem detects a communicative coupling of a cochlear implant associated with a patient to a sound processor connected to a fitting subsystem. The fitting subsystem may detect the communicative coupling in any of the ways described herein.

In step 704, the fitting subsystem automatically determines, in response to the communicative coupling, an implant side associated with the cochlear implant in accordance with one or more implant side selection factors. The determination may be performed in any of the ways described herein.

Various examples of automatically determining an implant side associated with a cochlear implant will now be provided. It will be recognized that the examples given herein are merely illustrative of the many different ways in which a fitting subsystem may automatically determine an implant side associated with a cochlear implant and that the scenarios associated with each of the examples are merely illustrative of the many different scenarios in which the methods and systems described herein may be employed.

Figure 8:
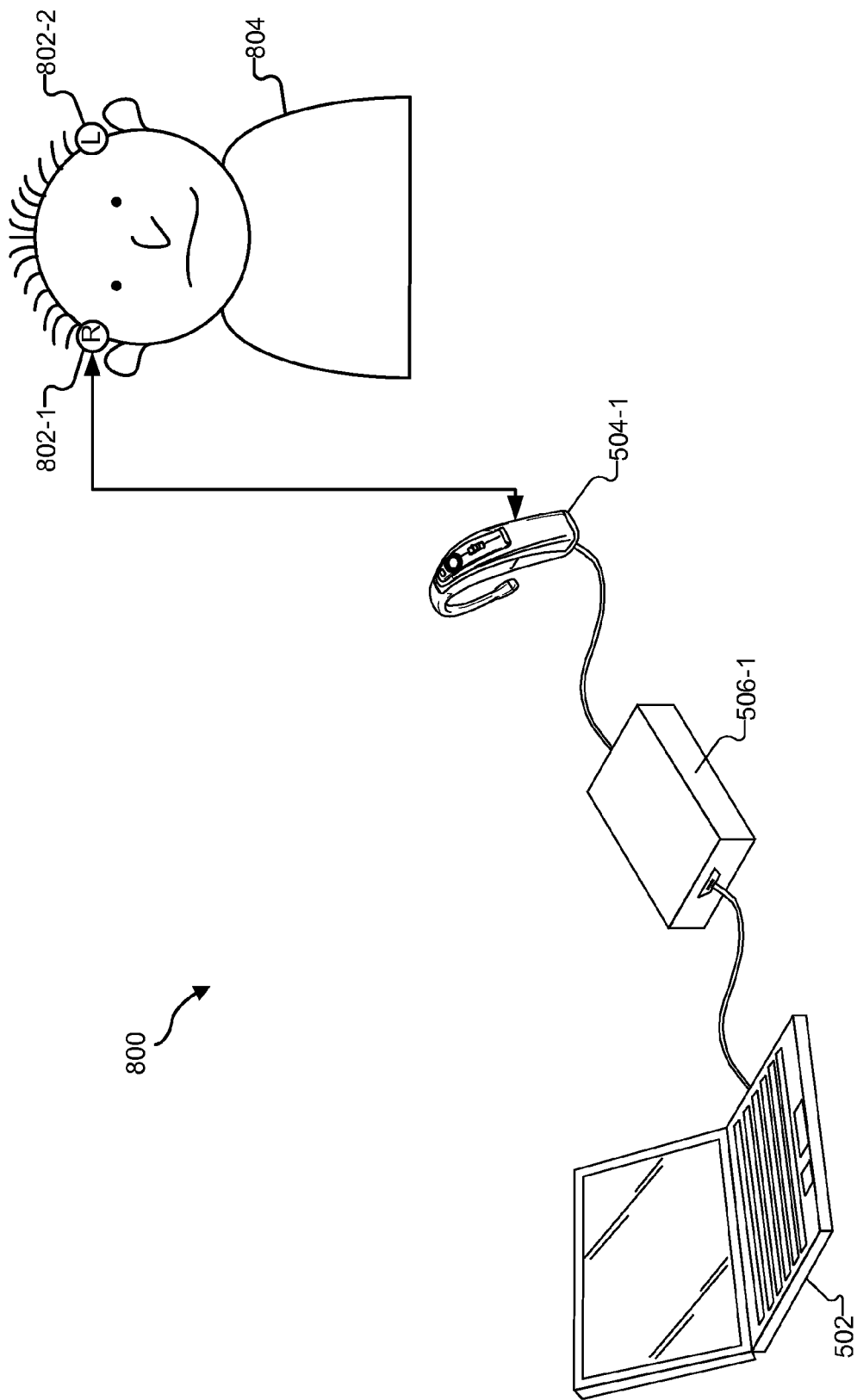
FIG. 8 illustrates an exemplary cochlear implant fitting scenario according to principles described herein.

FIG. 8 illustrates an exemplary scenario 800 in which a cochlear implant 802-1 is communicatively coupled to sound processor 504-1, which may be connected to fitting station 502 by way of CPI device 506-1, as described in connection with FIG. 5. As shown in FIG. 8, cochlear implant 802-1 is associated with a first ear (e.g., the right ear) of a patient 804. In some examples, as shown, patient 804 may have a second cochlear implant 802-2 associated with a second ear (e.g., the left ear). Cochlear implants 802-1 and 802-2 may be implanted in patient 804 using any suitable technique as may serve a particular implementation. Alternatively, patient 804 may only have a single cochlear implant (e.g., cochlear implant 802-1) implanted therein. Scenario 800 will be used to describe various ways in which fitting subsystem 202 may automatically determine an implant side associated with a cochlear implant.

In some examples, fitting subsystem 202 may automatically determine the implant side associated with a cochlear implant by determining that an implant record associated with the cochlear implant is stored by a sound processor to which the cochlear implant is communicatively coupled and obtaining data representative of the implant side from the implant record.

To illustrate, sound processor 504-1 may store an implant record associated with cochlear implant 802-1. The implant record may include at least some of the same information included in an implant record maintained by a fitting subsystem, and may be imported by a fitting subsystem not previously associated with patient 804 (e.g., by a fitting subsystem located at a clinic to which patient 804 has moved). For example, the implant record stored by sound processor 504-1 may include information indicating that cochlear implant 802-1 is associated with a right side of patient 804. Fitting station 502 may obtain data representative of the implant side associated with cochlear implant 802-1 by analyzing the implant record stored by sound processor 504-1, importing the implant record from sound processor 504-1, and/or in any other manner as may serve a particular implementation.

Additionally or alternatively, fitting subsystem 202 may automatically determine the implant side associated with a cochlear implant by determining that the sound processor to which the cochlear implant is communicatively coupled is formatted for a particular implant side and designating the implant side associated with the cochlear implant as being the particular implant side.

To illustrate, fitting station 502 may detect that sound processor 504-1 is formatted for the right side of patient 804 by analyzing program data and/or any other data associated with sound processor 504-1. Based on this information, fitting station 502 may determine that cochlear implant 802-1 is associated with the right side.

In some examples, fitting station 502 may determine that first and second active implant records are associated with patient 804 and that an implant record stored by sound processor 504-1 indicates the same implant side as the first implant record. Fitting station 502 may present an option to a user thereof to deactivate the first implant record (e.g., mark the first implant record as corresponding to an explanted cochlear implant) and replace it with the implant record stored by sound processor 504-1. Fitting station 502 may additionally or alternatively provide a warning that the determined implant side is already associated with another cochlear implant corresponding to the first implant record and that the first implant record will be marked to indicate that the another cochlear implant has been explanted in response to a confirmation of the determined implant side by the user.

Additionally or alternatively, fitting subsystem 202 may automatically determine the implant side associated with a cochlear implant by identifying an inactive implant record previously associated with the cochlear implant and maintained by fitting subsystem 202 and obtaining data representative of the implant side from the inactive implant record.

To illustrate, an implant record maintained by fitting station 502 and associated with cochlear implant 802-1 may be inadvertently modified or marked to indicate that cochlear implant 802-1 has been explanted and is no longer in use. Upon connection of cochlear implant 802-1 to sound processor 504-1, fitting station 502 may identify the inactive implant record as being previously associated with cochlear implant 802-1 (e.g., by matching a unique identifier of cochlear implant 802-1 to a unique identifier included in the inactive implant record). Data representative of the implant side of cochlear implant 802-1 may then be obtained by fitting station 502 from the inactive implant record. In some examples, fitting station 502 may be further configured to mark the inactive implant record as active.

Additionally or alternatively, fitting subsystem 202 may automatically determine the implant side associated with a cochlear implant used by a patient by determining that, during a single fitting session, an additional cochlear implant associated with the patient was communicatively coupled to the sound processor connected to fitting subsystem 202 prior to the cochlear implant being communicatively coupled to the sound processor, determining an implant side associated with the additional cochlear implant, and designating the implant side associated with the cochlear implant as being contralateral to the implant side associated with the additional cochlear implant.

To illustrate, fitting station 502 may determine that, during a particular fitting session, cochlear implant 802-2 was communicatively coupled to sound processor 504-1 prior to cochlear implant 802-1 being communicatively coupled to sound processor 504-1. Fitting station 502 may determine that cochlear implant 802-2 is associated with the left side of patient 804 (e.g., by analyzing an implant record associated with cochlear implant 802-2 and/or in any other manner). The likelihood of another cochlear implant that is associated with the left side being communicatively coupled to sound processor 504-1 during the same fitting session is relatively low. Therefore, fitting station 502 may automatically designate the implant side associated with cochlear implant 802-1 as being contralateral to the implant side associated with cochlear implant 802-2 (i.e., associated with the right side of patient 804).

Additionally or alternatively, fitting subsystem 202 may automatically determine the implant side associated with a cochlear implant used by a patient by determining that a single unassociated implant record exists (i.e., is maintained by fitting subsystem 202) for the patient and obtaining data representative of the implant side from the single unassociated implant record.

Figure 9:
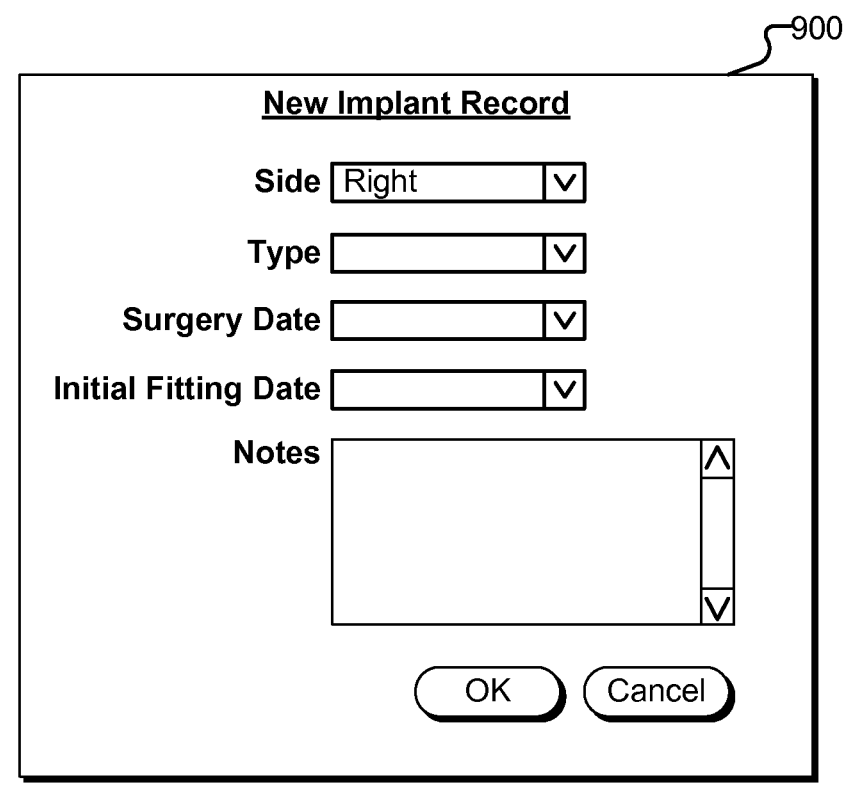

To illustrate, a user of fitting station 502 may manually create an implant record for patient 804 before patient 804 arrives at a clinic to be fitted. FIG. 9 illustrates an exemplary GUI 900 that may be displayed by fitting station 502 and that may be configured to facilitate manual creation of an implant record. As shown in FIG. 9, GUI 900 includes a plurality of fields into which data associated with a cochlear implant may be input by the user. For example, GUI 900 may be used by a user to input an implant side, type, surgery date, initial fitting date, and one or more notes associated with cochlear implant 802-1.

A manually created implant record is unassociated until a cochlear implant and its corresponding sound processor become communicatively coupled to fitting station 502. At this point, the unique identifier associated with the cochlear implant may be acquired from the cochlear implant and included in the manually created implant record. The implant record is then considered to be associated.

Hence, returning to FIG. 8, fitting station 502 may detect the existence of a single unassociated implant record associated with patient 804. Fitting station 502 may assume that the single unassociated implant record corresponds to cochlear implant 802-1 and obtain data representative of the implant side of cochlear implant 802-1 from the single unassociated implant record.

Additionally or alternatively, fitting subsystem 202 may automatically determine the implant side associated with a cochlear implant used by a patient by determining that a first unassociated implant record and a second unassociated implant record exist for the patient, determining that an implant type of the cochlear implant matches data included in only the first unassociated implant record, and obtaining data representative of the implant side from the first unassociated implant record.

To illustrate, a user of fitting station 502 may manually create unassociated implant records for two different types of cochlear implants, one of which may match the type of cochlear implant 802-1. Fitting station 502 may select the matching implant record for association with cochlear implant 802-1 and obtain data representative of the implant side from the selected implant record.

Additionally or alternatively, fitting subsystem 202 may automatically determine the implant side associated with a cochlear implant used by a patient by determining that a single associated implant record not associated with the cochlear implant exists for the patient and designating the implant side associated with the cochlear implant as being contralateral to an implant side designated by the single associated implant record.

To illustrate, fitting station 502 may determine that a single associated implant record not associated with cochlear implant 802-1 exists for patient 804. Because the single associated implant record is not associated with cochlear implant 802-1 (i.e., the implant record is associated with a different cochlear implant), fitting subsystem 202 may assume that cochlear implant 802-1 is associated with an implant side contralateral to that specified by the single associated implant record.

Additionally or alternatively, fitting subsystem 202 may automatically determine the implant side associated with a cochlear implant used by a patient by determining that no implant records exist for the patient and selecting, in response to the determination that no implant records exist for the patient, a default implant side as the implant side associated with the cochlear implant.

To illustrate, fitting station 502 may determine that no implant records exist for patient 804. In response, fitting station 502 may select a default implant side as the implant side associated with cochlear implant 504-1. The default implant side may be definable by the clinician. For example, marketing research may indicate that a majority of cochlear implants are associated with the right side of patients. Hence, the default implant side may be defined to be the right side.

In some examples, fitting station 502 may determine, based on a unique identifier associated with cochlear implant 802-1, that cochlear implant 802-1 belongs to a patient other than the patient associated with a patient file currently open by the fitting station 502. To illustrate, a clinician may have inadvertently opened a patient file associated with a patient other than patient 804. In this case, when cochlear implant 802-1 and sound processor 504-1 become communicatively coupled to fitting station 502, fitting station 502 may recognize that patient 804 is not the same as the patient associated with the opened patient file. Fitting station 502 may accordingly not allow automatic selection of an implant side associated with cochlear implant 802-1 and notify a user of fitting station 502 that patient 804 is not associated with the opened patient file.

In some examples, a cochlear implant emulation device may be selectively and communicatively coupled to sound processor 504-1. The term "cochlear implant emulation device," as used herein, refers to a device that is not implanted in a patient but that is configured to emulate a cochlear implant (e.g., cochlear implant 802-1). For example, a cochlear implant emulation device may include an implantable cochlear device (e.g., a cochlear implant) bundled with a resistive load. A cochlear implant emulation device may also be referred to as a "reference implant."

Figure 10:
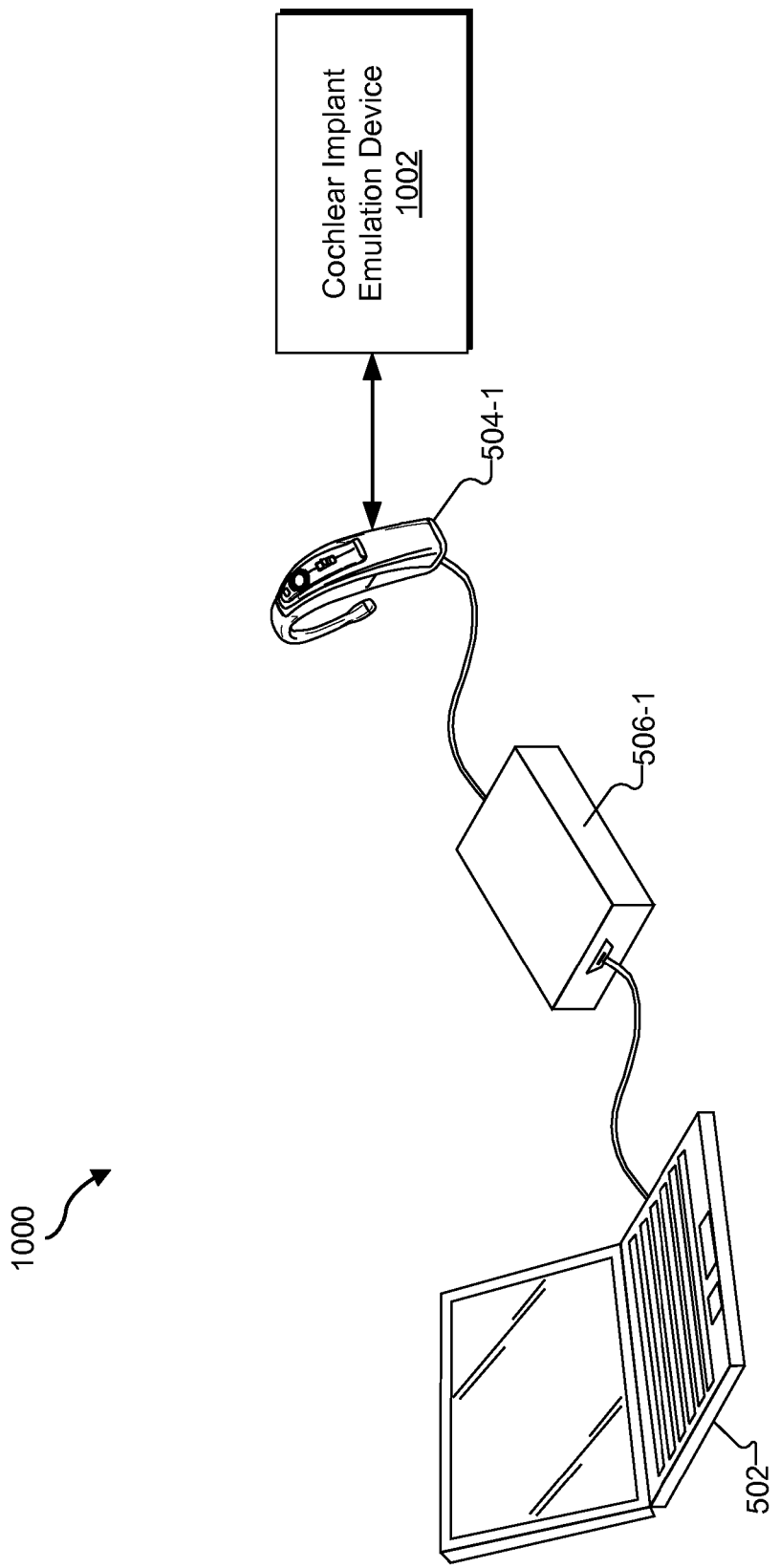
FIGS. 10-12 illustrate exemplary cochlear implant fitting scenarios according to principles described herein.

To illustrate, FIG. 10 illustrates an exemplary scenario 1000 in which a cochlear implant emulation device 1002 is communicatively coupled to sound processor 504-1 in place of cochlear implant 802-1. Cochlear implant emulation device 1002 may be used to perform diagnostic and/or troubleshooting procedures on a cochlear implant system. For example, if a cochlear implant system of which cochlear implant 802-1 is a part stops working correctly, cochlear implant emulation device 1002 may be substituted for cochlear implant 802-1, as shown in FIG. 10, in order to determine whether cochlear implant 802-1 is the source of a problem. Scenario 1000 will be used to describe various ways in which fitting subsystem 202 may automatically determine an implant side associated with a cochlear implant emulation device that has been communicatively coupled to fitting subsystem 202.

In some examples, fitting subsystem 202 may automatically determine the implant side associated with a cochlear implant emulation device by determining that a single associated implant record exists for a patient and obtaining data representative of the implant side from the single associated implant record.

To illustrate, fitting station 502 may determine that a single associated implant record associated with cochlear implant 802-1 and corresponding to patient 804 exists within a database maintained or otherwise used by fitting station 502. Fitting station 502 may therefore assume that cochlear implant emulation device 1002 has replaced cochlear implant 802-1 and designate cochlear implant emulation device 1002 as being associated with the same implant side with which cochlear implant 802-1 is associated. To this end, fitting station 502 may obtain data representative of the implant side from the single associated implant record associated with cochlear implant 802-1.

Additionally or alternatively, fitting subsystem 202 may automatically determine the implant side associated with a cochlear implant emulation device by determining that two associated implant records exist for a patient, determining that no other cochlear implant associated with the patient is communicatively coupled to fitting subsystem 202 while the cochlear implant emulation device is communicatively coupled to a sound processor that is connected to fitting subsystem 202, and selecting, in response to the determination that no other cochlear implant associated with the patient is communicatively coupled to fitting subsystem 202, a default implant side as the implant side associated with the cochlear implant emulation device.

To illustrate, fitting station 502 may determine that two associated implant records exist for patient 804. Fitting station 502 may further determine that no other cochlear implants other than cochlear implant emulation device 1002 are communicatively coupled to fitting station 502. In response, fitting station 502 may select a default implant side as the implant side associated with cochlear implant emulation device 1002.

In some examples, in response to a communicative coupling of cochlear implant emulation device 1002 to sound processor 504-1, fitting station 502 may determine that no associated implant records exist for a patient. In these instances, fitting station 502 may abstain from designating an implant side for cochlear implant emulation device 1002.

Figure 11:
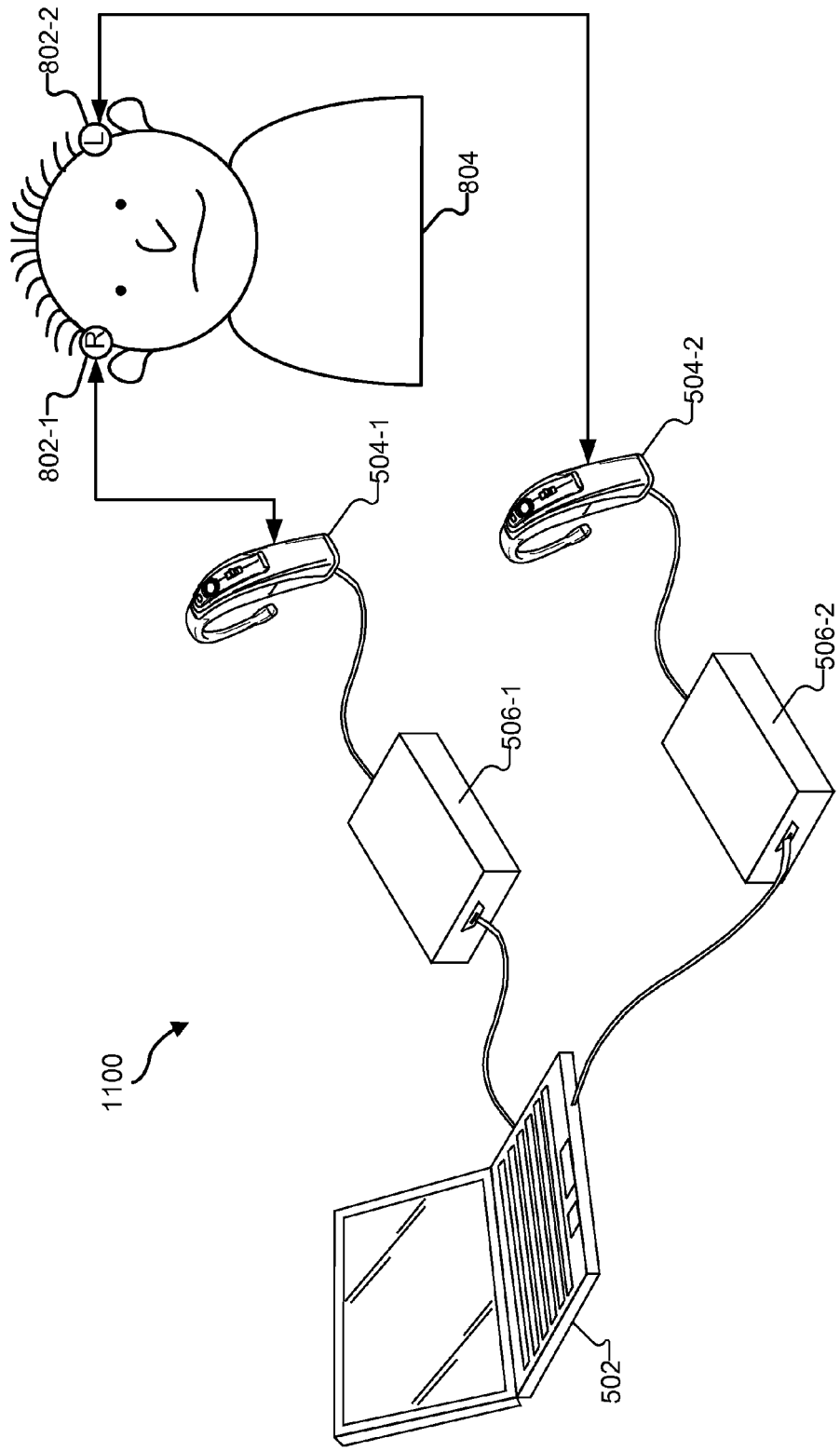

FIG. 11 illustrates an exemplary scenario 1100 in which a first cochlear implant 802-1 is communicatively coupled to sound processor 504-1 and a second cochlear implant 802-2 is communicatively coupled to sound processor 504-2. Sound processors 504-1 and 504-2 may be connected to fitting station 502 by way of CPI devices 506-1 and 506-2, as described in connection with FIG. 6. As shown in FIG. 11, cochlear implant 802-1 is associated with a first ear (e.g., the right ear) of patient 804 and cochlear implant 802-2 is associated with a second ear (e.g., the left ear) of patient 804. Scenario 1100 is illustrative of a scenario in which a bilateral cochlear implant patient may be fitted by fitting station 502 and will be used to describe an additional way in which fitting subsystem 202 may automatically determine an implant side associated with a cochlear implant.

In some examples, fitting subsystem 202 may automatically determine the implant side associated with a first cochlear implant communicatively coupled to a first sound processer connected to fitting subsystem 202 by determining that a second cochlear implant associated with a patient is concurrently and communicatively coupled to a second sound processor connected to fitting subsystem 202, determining an implant side associated with the second cochlear implant, and designating the implant side associated with the first cochlear implant as being contralateral to the implant side associated with the second cochlear implant.

To illustrate, fitting station 502 may determine that first cochlear implant 802-1 and second cochlear implant 802-2 are concurrently and communicatively coupled to fitting station 502 by way of first sound processor 504-1 and second sound processor 504-2, respectively. Fitting station 502 may determine that second cochlear implant 802-2 is associated with the left side of patient 804 by analyzing an implant record associated with second cochlear implant 802-2 and/or in any other suitable manner. Fitting station 502 may then assume that first cochlear implant 802-1 is associated with the contralateral side (i.e., the right side of patient 804) and designate first cochlear implant 802-1 as such.

Figure 12:
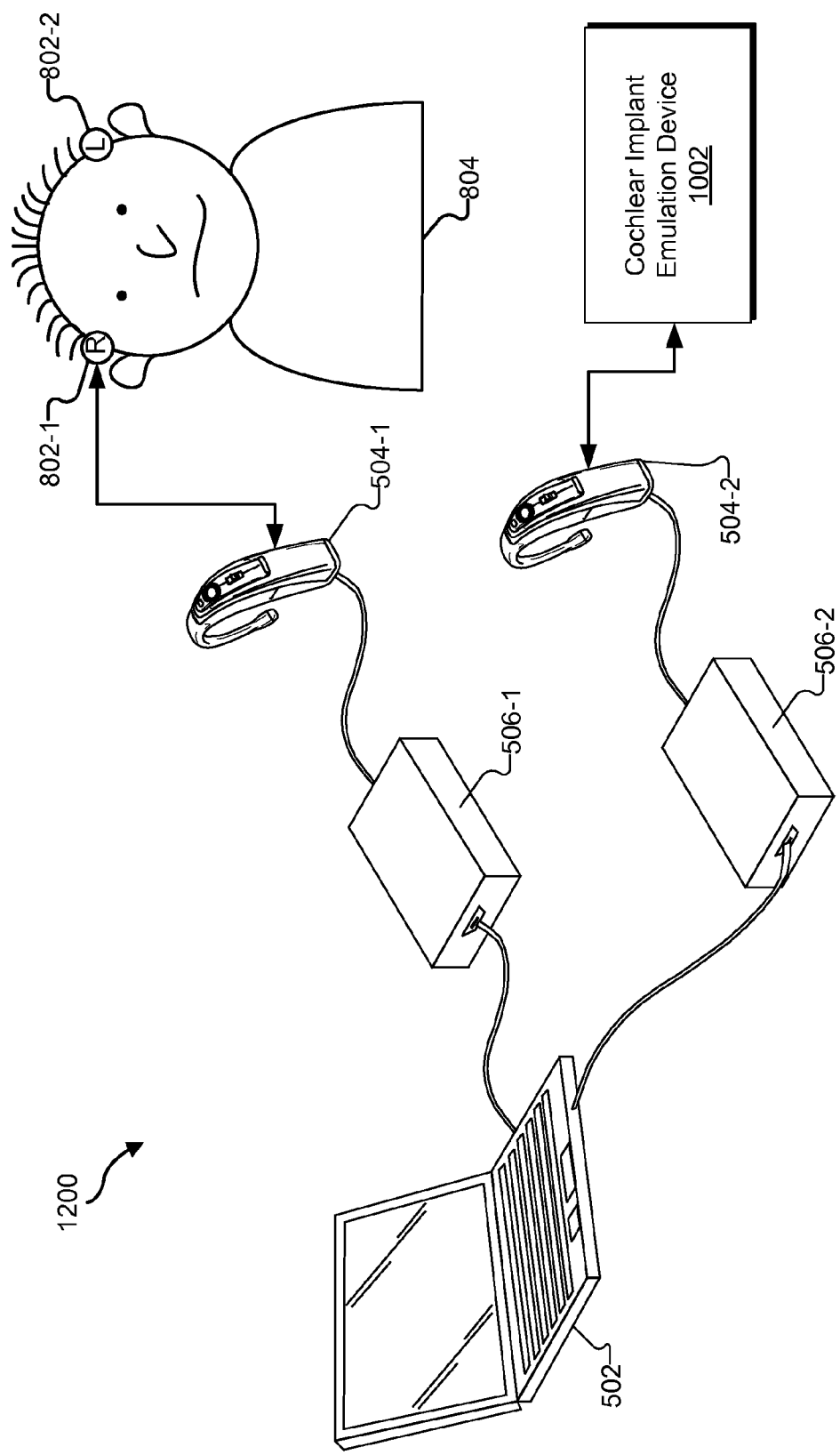

FIG. 12 illustrates an exemplary scenario 1200 in which cochlear implant emulation device 1002 has replaced second cochlear implant 802-2 as being communicatively coupled to sound processor 504-2. Hence, scenario 1200 represents a modified version of scenario 1100 shown in FIG. 11. Scenario 1200 will be used to describe an additional way in which fitting subsystem 202 may automatically determine an implant side associated with a cochlear implant emulation device.

In some examples, fitting subsystem 202 may automatically determine the implant side associated with a cochlear implant emulation device by determining that two associated implant records exist for a patient, determining that a cochlear implant associated with the patient is communicatively coupled to a first sound processor connected to fitting subsystem 202 while the cochlear implant emulation device is communicatively coupled to a second sound processor, determining, based on one of the two associated implant records that is associated with the cochlear implant, an implant side associated with the cochlear implant, and designating the implant side associated with the cochlear implant emulation device as being contralateral to the implant side associated with the cochlear implant.

To illustrate, fitting station 502 may determine that cochlear implant 802-1 is communicatively coupled to sound processor 504-1 while cochlear implant emulation device 1002 is communicatively coupled to sound processor 504-2. Fitting station 502 may further determine that two associated implant records exist for patient 804. Fitting station 502 may analyze one of the two associated implant records that is associated with cochlear implant 802-1 to determine that cochlear implant 802-1 is associated with the right side of patient 804. Fitting station 502 may then assume that cochlear implant emulation device 1002 is associated with the contralateral side (i.e., the left side of patient 804) and designate cochlear implant emulation device 1002 as such.

Figure 13:
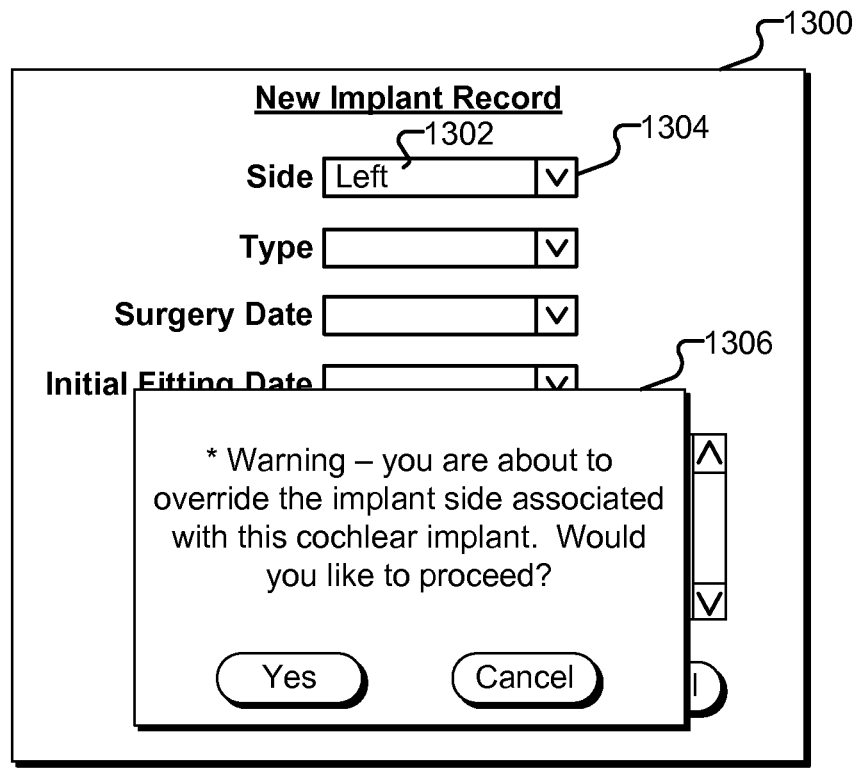
FIG. 13 illustrates an exemplary GUI configured to facilitate overriding of an automatically determined implant side for a cochlear implant according to principles described herein.

In some examples, in response to an automatic determination of a fitting side associated with a cochlear implant, fitting subsystem 202 may automatically populate an implant record associated with the cochlear implant with data representative of the determined implant side. Fitting subsystem 202 may be further configured to provide an override option configured to allow a user to override the determined implant side by selecting a different implant side to be associated with the cochlear implant. The override option may be provided within a GUI, for example. To illustrate, FIG. 13 illustrates an exemplary GUI 1300 that may be provided for display and configured to facilitate overriding of an automatically determined implant side for a particular cochlear implant. As shown in FIG. 13, an implant side field 1302 may be automatically populated with a determined implant side. A user may select a down arrow 1304 to override the determined implant side and select a different implant side to be associated with the cochlear implant. In response, a warning message 1306 may be displayed within GUI 1300 warning the user that he or she is about to override the implant side associated with the cochlear implant. Fitting subsystem 202 may facilitate overriding of an automatically determined implant side in any other way as may serve a particular implementation.

Figure 14:
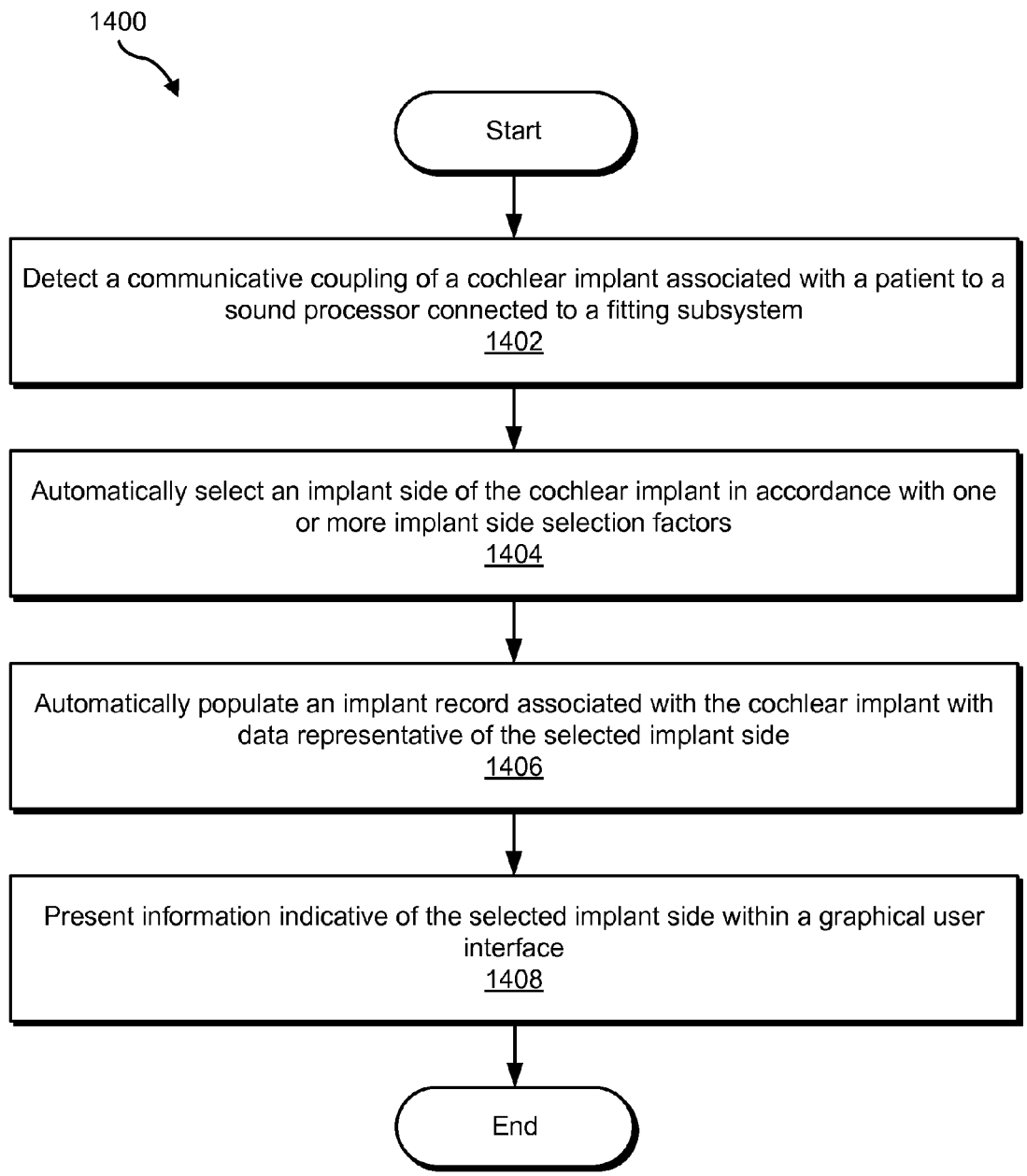
FIG. 14 illustrates another exemplary method of automatically determining an implant side associated with a cochlear implant according to principles described herein.

FIG. 14 illustrates another exemplary method 1400 of automatically determining an implant side associated with a cochlear implant. While FIG. 14 illustrates exemplary steps according to one embodiment, other embodiments may omit, add to, reorder, and/or modify any of the steps shown in FIG.

14. One or more of the steps shown in FIG. 14 may be performed by any component or combination of components of fitting subsystem 202 and/or fitting station 502.

In step 1402, a communicative coupling of a cochlear implant associated with a patient to a sound processor connected to a fitting subsystem is detected. Step 1402 may be performed in any of the ways described herein.

In step 1404, an implant side of the cochlear implant is automatically select in accordance with one or more implant side selection factors. Step 1404 may be performed in any of the ways described herein.

In step 1406, an implant record associated with the cochlear implant is automatically populated with data representative of the selected implant side. Step 1406 may be performed in any of the ways described herein.

In step 1408, information indicative of the selected implant side is presented within a graphical user interface. Step 1408 may be performed in any of the ways described herein.

In certain embodiments, one or more of the components and/or processes described herein may be implemented and/or performed by one or more appropriately configured computing devices. To this end, one or more of the systems and/or components described above may include or be implemented by any computer hardware and/or computer-implemented instructions (e.g., software) embodied on a non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known non-transitory computer-readable media.

A non-transitory computer-readable medium (also referred to as a processor-readable medium) includes any non-transitory medium that participates in providing data (e.g., instructions) that may be read by a computer (e.g., by a processor of a computer). Such a non-transitory medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of non-transitory computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other non-transitory medium from which a computer can read.

Figure 15:
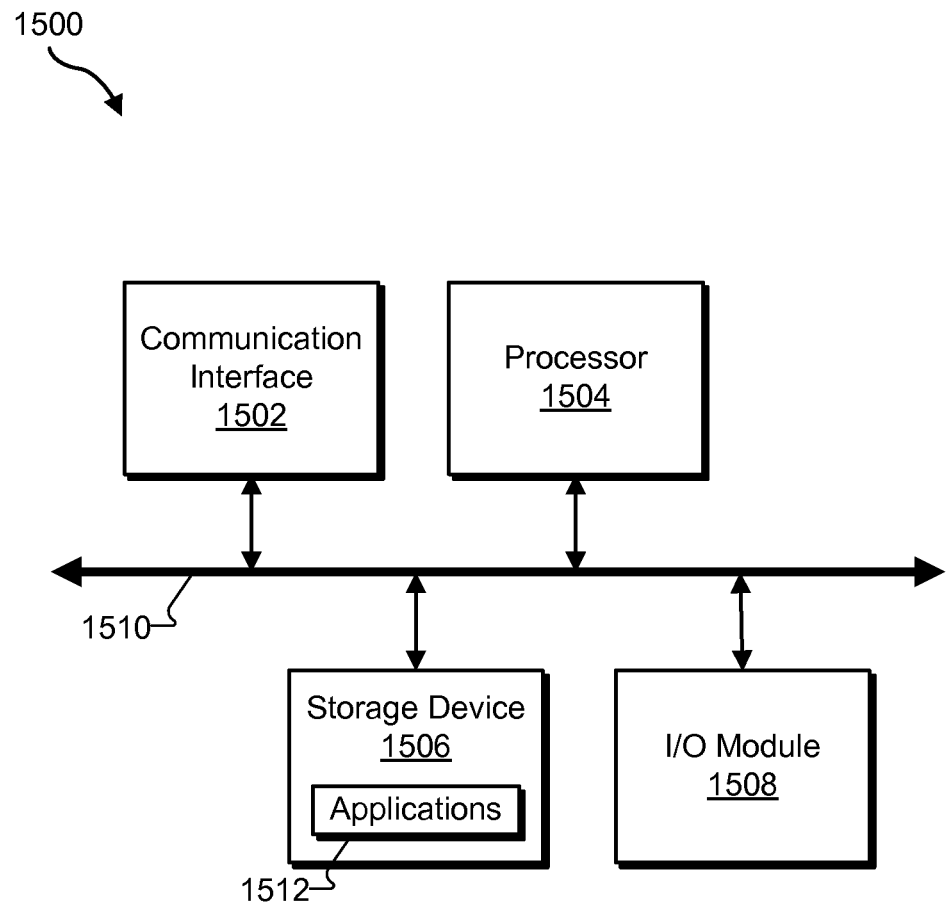
FIG. 15 illustrates an exemplary computing device according to principles described herein.

FIG. 15 illustrates an exemplary computing device 1500 that may be configured to perform one or more of the processes described herein. As shown in FIG. 15, computing device 1500 may include a communication interface 1502, a processor 1504, a storage device 1506, and an input/output ("I/O") module 1508 communicatively connected via a communication infrastructure 1510. While an exemplary computing device 1500 is shown in FIG. 15, the components illustrated in FIG. 15 are not intended to be limiting. Additional or alternative components may be used in other embodiments. Components of computing device 1500 shown in FIG. 15 will now be described in additional detail.

Communication interface 1502 may be configured to communicate with one or more computing devices. Examples of communication interface 1502 include, without limitation, a wired network interface (such as a network interface card), a wireless network interface (such as a wireless network interface card), a modem, and any other suitable interface. Communication interface 1502 may additionally or alternatively provide such a connection through, for example, a local area network (such as an Ethernet network), a personal area network, a telephone or cable network, a satellite data connection, a dedicated URL, or any other suitable connection. Communication interface 1502 may be configured to interface with any suitable communication media, protocols, and formats, including any of those mentioned above.

Processor 1504 generally represents any type or form of processing unit capable of processing data or interpreting, executing, and/or directing execution of one or more of the instructions, processes, and/or operations described herein. Processor 1504 may direct execution of operations in accordance with one or more applications 1512 or other computer-executable instructions such as may be stored in storage device 1506 or another non-transitory computer-readable medium.

Storage device 1506 may include one or more data storage media, devices, or configurations and may employ any type, form, and combination of data storage media and/or device. For example, storage device 1506 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1506. For example, data representative of one or more executable applications 1512 (which may include, but are not limited to, one or more of the software applications described herein) configured to direct processor 1504 to perform any of the operations described herein may be stored within storage device 1506. In some examples, data may be arranged in one or more databases residing within storage device 1506.

I/O module 1508 may be configured to receive user input and provide user output and may include any hardware, firmware, software, or combination thereof supportive of input and output capabilities. For example, I/O module 1508 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1508 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1508 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1500. For example, one or more applications 1512 residing within storage device 1506 may be configured to direct processor 1504 to perform one or more processes or functions associated with communication facility 302, user interface facility 304, fitting facility 306, detection facility 308, implant side management facility 310, communication facility 402, and/or processing facility 404. Likewise, storage facility 312 and/or storage facility 406 may be implemented by or within storage device 1506.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
    detecting, by a fitting subsystem, a communicative coupling of a cochlear implant associated with a patient to a sound processor connected to the fitting subsystem by receiving a signal from the cochlear implant indicating that the cochlear implant is communicatively coupled to the sound processor;
    automatically determining, by the fitting subsystem in response to the communicative coupling, an implant side associated with the cochlear implant in accordance with one or more implant side selection factors;
    automatically populating, by the fitting subsystem, an implant record associated with the cochlear implant with data representative of the determined implant side, and
    presenting, by the fitting subsystem within a graphical user interface and in response to the automatically populating, at least a portion of the implant record associated with the cochlear implant and automatically populated with data representative of the determined implant side.

2. The method of claim 1, further comprising providing, by the fitting subsystem within the graphical user interface, an override option configured to allow a user to override the determined implant side by selecting a different implant side to be associated with the cochlear implant.

3. The method of claim 2, further comprising providing, by the fitting subsystem within the graphical user interface, an option to designate another cochlear implant previously associated with the different implant side as being explanted.

4. The method of claim 1, wherein the automatically determining of the implant side associated with the cochlear implant comprises:
    determining that an additional implant record associated with the cochlear implant is stored by the sound processor; and
    obtaining data representative of the implant side from the additional implant record.

5. The method of claim 4, further comprising importing, by the fitting subsystem, the additional implant record from the sound processor.

6. The method of claim 1, wherein the automatically determining of the implant side associated with the cochlear implant comprises:
    identifying an inactive implant record previously associated with the cochlear implant and maintained by the fitting subsystem; and
    obtaining data representative of the implant side from the inactive implant record.

7. The method of claim 6, further comprising marking, by the fitting subsystem in response to the identifying of the inactive implant record, the inactive implant record as active.

8. The method of claim 1, wherein the cochlear implant comprises a cochlear implant emulation device and wherein the automatically determining of the implant side associated with the cochlear implant comprises:
    determining that a single associated implant record exists for the patient; and
    obtaining data representative of the implant side from the single associated implant record.

9. The method of claim 1, wherein the cochlear implant comprises a cochlear implant emulation device and wherein the automatically determining of the implant side associated with the cochlear implant comprises:
    determining that two associated implant records exist for the patient;
    determining, in response to the determining that the two associated implant records exist for the patient, that an additional cochlear implant associated with the patient is communicatively coupled to an additional sound processor connected to the fitting subsystem while the cochlear implant emulation device is communicatively coupled to the sound processor;
    determining, based on one of the two associated implant records that is associated with the additional cochlear implant, an implant side associated with the additional cochlear implant; and
    designating the implant side associated with the cochlear implant emulation device as being contralateral to the implant side associated with the additional cochlear implant.

10. The method of claim 1, wherein the cochlear implant comprises a cochlear implant emulation device and wherein the automatically determining of the implant side associated with the cochlear implant comprises:
    determining that two associated implant records exist for the patient;
    determining, in response to the determining that the two associated implant records exist for the patient, that no other cochlear implant associated with the patient is communicatively coupled to the fitting subsystem while the cochlear implant emulation device is communicatively coupled to the sound processor; and
    selecting, in response to the determination that no other cochlear implant associated with the patient is communicatively coupled to the fitting subsystem, a default implant side as the implant side associated with the cochlear implant emulation device.

11. The method of claim 1, wherein the automatically determining of the implant side associated with the cochlear implant comprises:
    determining that an additional cochlear implant associated with the patient is communicatively coupled to an additional sound processor connected to the fitting subsystem while the cochlear implant is communicatively coupled to the sound processor;
    determining an implant side associated with the additional cochlear implant; and
    designating the implant side associated with the cochlear implant as being contralateral to the implant side associated with the additional cochlear implant.

12. The method of claim 1, wherein the automatically determining of the implant side associated with the cochlear implant comprises:
    determining that, during a single fitting session, an additional cochlear implant associated with the patient was communicatively coupled to the sound processor prior to the cochlear implant being communicatively coupled to the sound processor;

determining an implant side associated with the additional cochlear implant; and designating the implant side associated with the cochlear implant as being contralateral to the implant side associated with the additional cochlear implant.

13. The method of claim 1, wherein the automatically determining of the implant side associated with the cochlear implant comprises:

determining that a single unassociated implant record exists for the patient; and obtaining data representative of the implant side from the single unassociated implant record.

14. The method of claim 13, further comprising marking the single unassociated implant record as an associated implant record.

15. The method of claim 1, wherein the automatically determining of the implant side associated with the cochlear implant comprises:

determining that two unassociated implant records exist for the patient;

determining, in response to the determining that the two unassociated implant records exist for the patient, that a cochlear implant emulation device is communicatively coupled to an additional sound processor connected to the fitting subsystem while the cochlear implant is communicatively coupled to the sound processor;

determining an implant side associated with the cochlear implant emulation device; and designating the implant side associated with the cochlear implant as being contralateral to the implant side associated with the cochlear implant emulation device.

16. The method of claim 1, wherein the automatically determining of the implant side associated with the cochlear implant comprises:

determining that a first unassociated implant record and a second unassociated implant record exist for the patient;

determining that an implant type of the cochlear implant matches data included in only the first unassociated implant record; and obtaining data representative of the implant side from the first unassociated implant record.

17. The method of claim 1, wherein the automatically determining of the implant side associated with the cochlear implant comprises:

determining that the sound processor is formatted for a particular implant side; and designating the implant side associated with the cochlear implant as being the particular implant side.

18. The method of claim 1, wherein the automatically determining of the implant side associated with the cochlear implant comprises:

determining that no implant records exist for the patient; and selecting, in response to the determination that no implant records exist for the patient, a default implant side as the implant side associated with the cochlear implant.

19. The method of claim 1, wherein the automatically determining of the implant side associated with the cochlear implant comprises:

determining that a single associated implant record not associated with the cochlear implant exists for the patient; and designating the implant side associated with the cochlear implant as being contralateral to an implant side specified by the single associated implant record.

20. The method of claim 1, further comprising providing, by the fitting subsystem within a graphical user interface, a warning that the determined implant side is already associated with another cochlear implant and that an implant record corresponding to the another cochlear implant will be marked to indicate that the another cochlear implant has been explanted in response to a confirmation of the determined implant side by a user.

21. The method of claim 1, embodied as computer-executable instructions on at least one non-transitory computer-readable medium.

22. The method of claim 1, wherein the automatically populating of the implant record associated with the cochlear implant with data representative of the determined implant side comprises:

determining that an additional implant record that includes the data representative of the determined implant side is stored by the sound processor; and importing, in response to the determining, the additional implant record from the sound processor.

23. A method comprising:

detecting, by a fitting subsystem, a communicative coupling of a cochlear implant associated with a patient to a sound processor connected to the fitting subsystem by receiving a signal from the cochlear implant indicating that the cochlear implant is communicatively coupled to the sound processor;

automatically selecting, by the fitting subsystem in response to the communicative coupling, an implant side of the cochlear implant in accordance with one or more implant side selection factors;

automatically populating, by the fitting subsystem, an implant record associated with the cochlear implant with data representative of the selected implant side; and presenting, by the fitting subsystem within a graphical user interface and in response to the automatically populating, at least a portion of the implant record associated with the cochlear implant and automatically populated with data representative of the selected implant side.

24. A system comprising:

a detection facility configured to detect a communicative coupling of a cochlear implant associated with a patient to a sound processor connected to a fitting station by receiving a signal from the cochlear implant indicating that the cochlear implant is communicatively coupled to the sound processor;

an implant side management facility communicatively coupled to the detection facility and configured to automatically determine, in response to the communicative coupling, an implant side associated with the cochlear implant in accordance with one or more implant side selection factors and to automatically populate an implant record associated with the cochlear implant with data representative of the determined implant side; and a user interface facility communicatively coupled to the implant side management facility and configured to present, within a graphical user interface and in response to the automatic population of the implant record, at least a portion of the implant record associated with the cochlear implant and automatically populated with data representative of the determined implant side.

* * * * *